United States Patent [19]
Amerov et al.

[11] Patent Number: 6,026,314
[45] Date of Patent: Feb. 15, 2000

[54] METHOD AND DEVICE FOR NONINVASIVE MEASUREMENTS OF CONCENTRATIONS OF BLOOD COMPONENTS

[75] Inventors: Airat K. Amerov, Yongin; Kye-jin Jeon; Yoen-joo Kim, both of Seoul; Gil-won Yoon, Sungnam, all of Rep. of Korea

[73] Assignee: Samsung Electronics Co., Ltd., Kyungki-Do, Rep. of Korea

[21] Appl. No.: 09/149,219

[22] Filed: Sep. 8, 1998

[30] Foreign Application Priority Data

Sep. 5, 1997 [KR] Rep. of Korea ............... 97-45970
Jun. 12, 1998 [KR] Rep. of Korea ............... 98-21969

[51] Int. Cl.$^7$ .................................................. A61B 5/00
[52] U.S. Cl. .................................. 600/322; 600/316
[58] Field of Search .................................. 600/310, 316, 600/322, 323, 326, 328, 473, 476

[56] References Cited

U.S. PATENT DOCUMENTS

| | | |
|---|---|---|
| 3,958,560 | 5/1976 | March . |
| 4,267,844 | 5/1981 | Yamanishi . |
| 4,805,623 | 2/1989 | Jobsis . |
| 4,901,728 | 2/1990 | Hutchinson . |
| 5,009,230 | 4/1991 | Hutchinson . |
| 5,028,787 | 7/1991 | Rosenthal et al. . |
| 5,243,893 | 9/1993 | Evans et al. . |
| 5,246,004 | 9/1993 | Clarke et al. . |
| 5,313,941 | 5/1994 | Braig et al. . |
| 5,435,309 | 7/1995 | Thomas . |
| 5,553,613 | 9/1996 | Parker . |
| 5,553,615 | 9/1996 | Carim et al. ........................ 600/324 |

FOREIGN PATENT DOCUMENTS

95/10038 4/1995 WIPO .

*Primary Examiner*—Eric F. Winakur
*Attorney, Agent, or Firm*—Kile, McIntyre, Harbin & Lee; Eugene M. Lee

[57] ABSTRACT

A method and device for noninvasive measurement of blood component concentrations utilizes pulsed polychromatic light source emitting, light in the near infrared range 800–1850 nm. The light is back scattered from or transmitted through a part of a patient's body. Back scattered light from blood-containing tissues and blood vessels has information on blood component concentrations. That light is collected to avoid the surface reflection from the skin surface and to minimize the effects of changes in the scattering background. The concentrations of blood components are calculated from the spectral analysis based on selected wavelengths by a defined algorithm. A microprocessor calculates and determines the blood component concentrations by comparing a ratio with a calibration curve stored in a memory of the microprocessor. The calculated concentration values are displayed on a display.

24 Claims, 4 Drawing Sheets

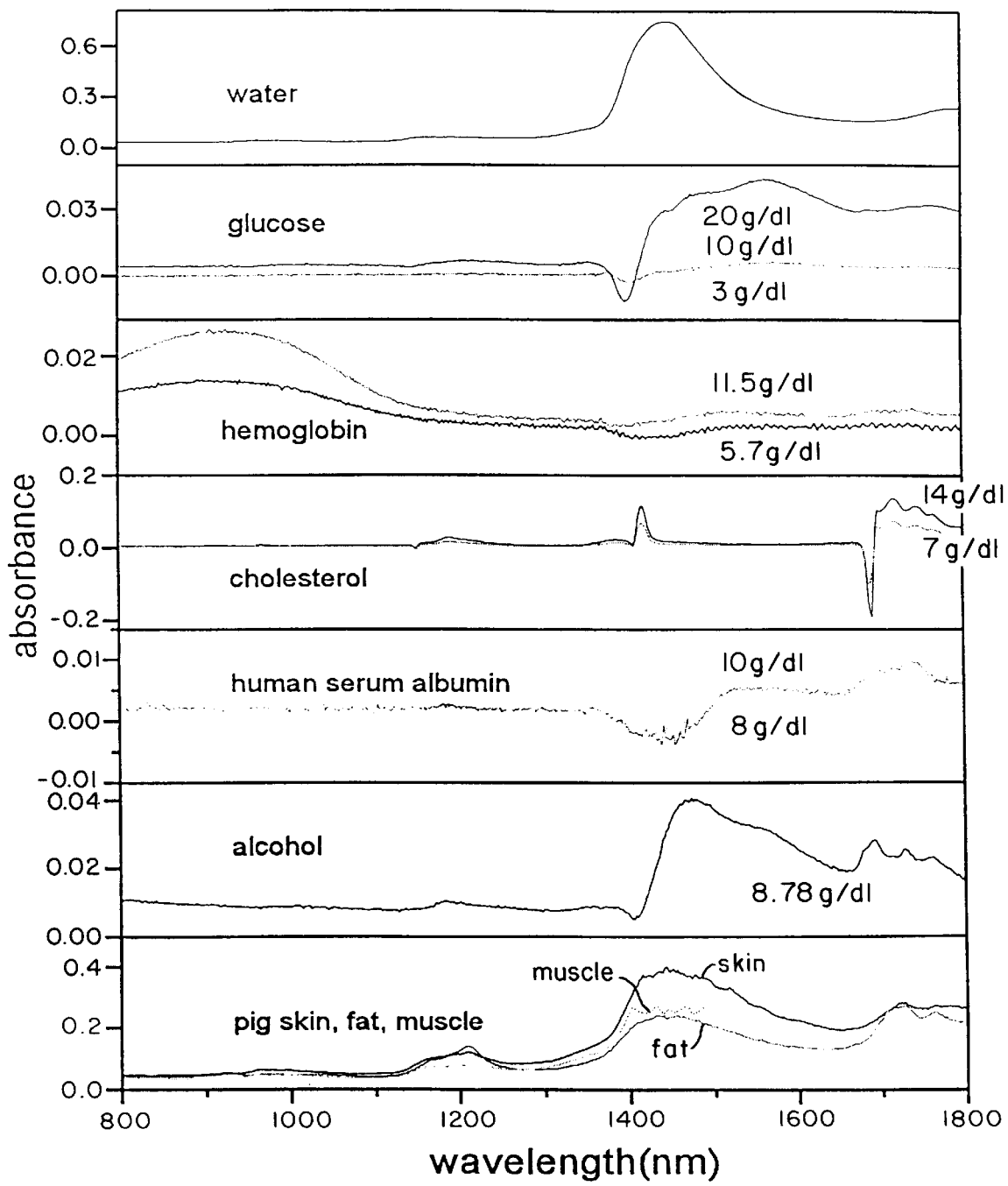
F I G. 1

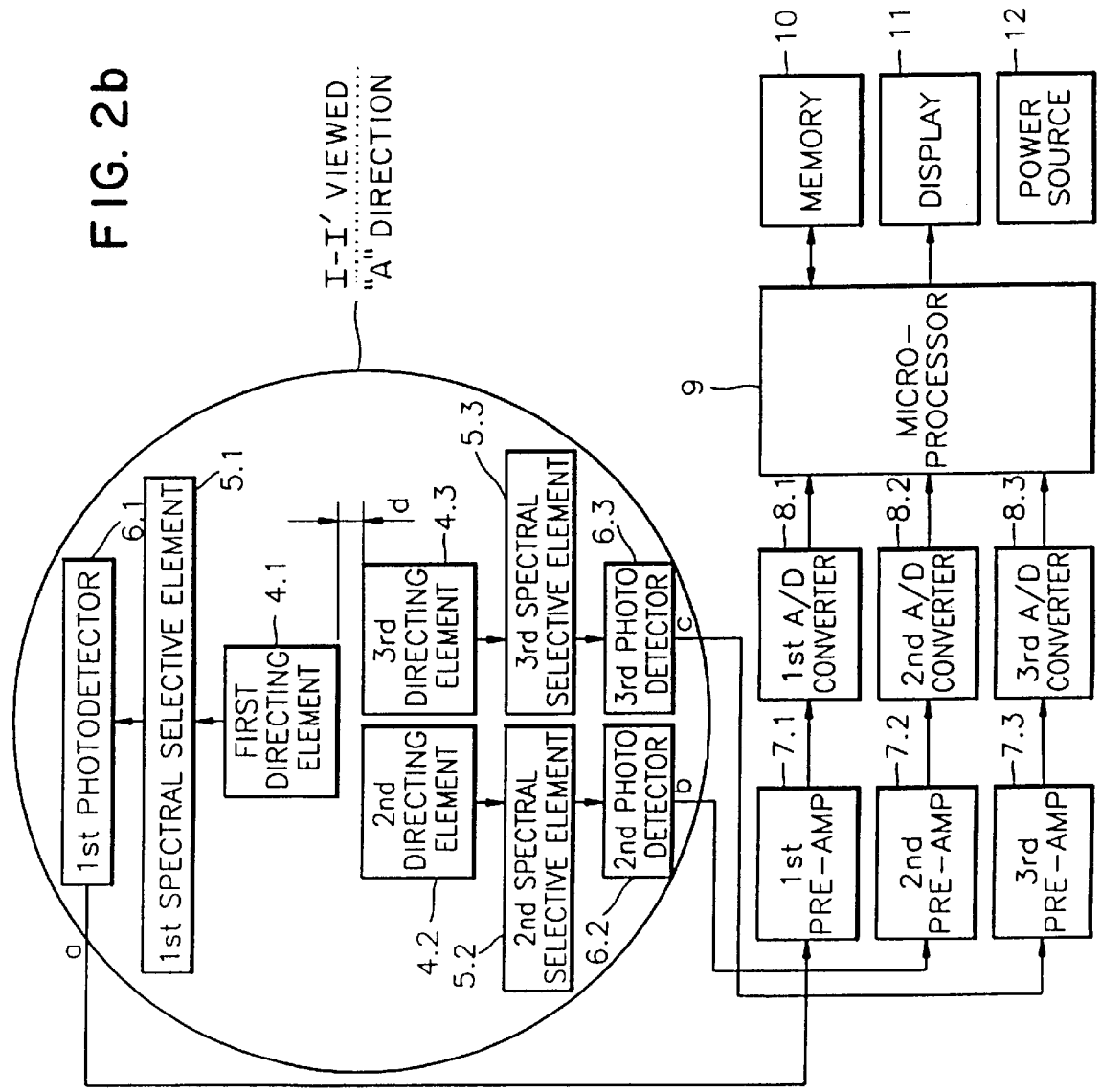

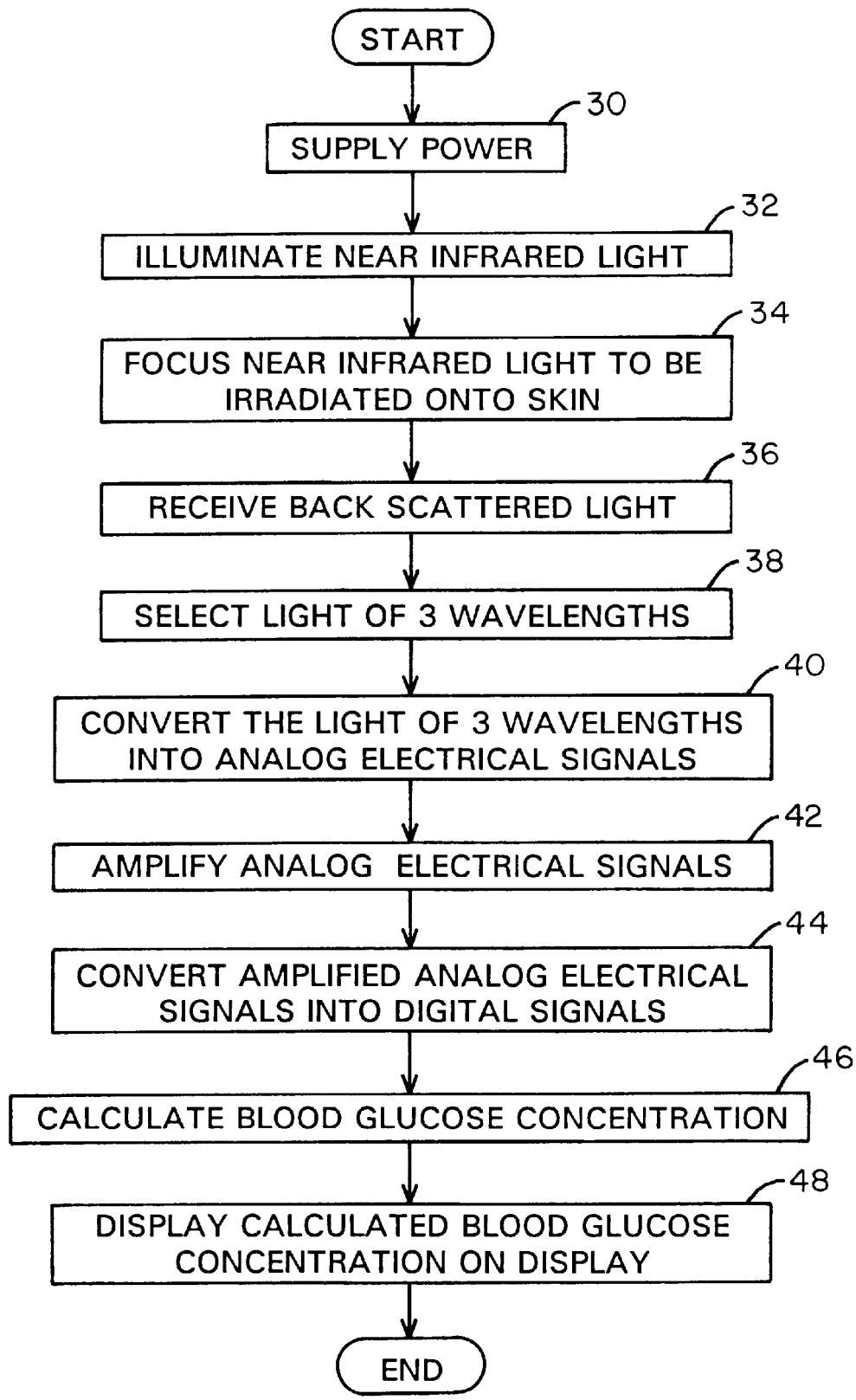
F I G. 3

METHOD AND DEVICE FOR NONINVASIVE MEASUREMENTS OF CONCENTRATIONS OF BLOOD COMPONENTS

BACKGROUND OF THE INVENTION

1. Field of the Invention

The present invention relates to a method and device for measuring blood component concentrations, and more particularly, to a noninvasive method and device for measuring blood component concentrations for components such as glucose, cholesterol, albumin, hemoglobin and bilirubin and some other analytes like alcohol and drugs based on spectroscopy.

2. Description of the Related Art

Previous devices for monitoring blood component concentrations of a patient are known. These devices typically use a small blood sample by pricking the tip of a finger which is placed on a chemically treated carrier and is inserted into a portable instrument to measure blood component concentrations. This finger prick is painful and can be a problem when samples are required often. Moreover, although the cost of these instruments is not significant, the cost for the disposable items (test strips, lancets and so on) and the health risks associated with having an open wound is not desirable. Moreover, the time interval between the moment the blood sample is placed on a chemically treated carrier and the moment the carrier is inserted into an instrument is critical and is a source of inaccuracy. Accordingly, there is a widespread demand for noninvasive determination of glucose for millions of diabetics all over the world. Many of them need several glucose tests each day to provide correct insulin control and diet. Noninvasive bilirubin measurements are useful for newborns with jaundice and cholesterol measurements are useful for people who suffer from arteriosclerosis.

Various schemes have been attempted to measure blood component concentrations in a noninvasive manner. Among them, U.S. Pat. Nos. 4,901,728 and 5,009,230 use an optical activity property of glucose and a rotation angle of the polarization is measured when a polarized light beam passes through a vascularized part of the body. The accuracy of the measurement is limited by small absorption of glucose in the range of 940–1000 nm and the existence of other components with optical activity properties in the human body (for example, some amino acids).

Another technique uses noninvasive sensor systems for glucose monitoring of the aqueous humor of the eye on the basis of polarization as shown by March, U.S. Pat. No. 3,958,560 or Raman spectroscopy (Tarr et al., U.S. Pat. No. 5,243,983). Unfortunately, these techniques may cause considerable discomfort to the patient because of the need to place a device on the patient's eye. A more accurate and less intrusive system is desired.

Another spectroscopic approach is based on near infrared absorption or reflection spectroscopy. Several of the references mentioned above utilize absorption or reflection spectroscopy to measure the glucose concentration in the human blood. The basic principle is to send light of several wavelengths into subcutaneous tissue containing blood and to detect the intensity of the light reflected or transmitted through the tissue. Using well developed mathematical algorithms, it is possible to calculate the glucose concentration from the light intensity values. The near infrared region of the spectrum is suitable for noninvasive measurement of concentrations of blood components because of the relatively good light transmission of skin tissues at these wavelengths. The main disadvantages of this approach are the low concentration of glucose in tissue relative to water that has significant absorption in this region; several other components in tissue interfering with glucose in light absorption; significantly non-homogeneous tissue structure and corresponding non-homogeneous distribution of glucose in tissue; light scattering properties of tissue influence on the quantitative light absorption measurements. Thus, the right choice for measurement of spectral range and the rules of wavelength selections are important to provide accuracy in glucose concentration determination.

The spectral range 800–1850 nm is suitable for performing quantitative measurements because in this range, the water absorption line at 1450 nm does not significantly overlap with absorption lines of other components such as protein, fat, hemoglobin, oxy-hemoglobin and at the same time it is possible to select a separate glucose absorption line in the vicinity of 1600 nm.

Constituents absorption in this region is greater than, for example, in the range 600–100 nm which is used in U.S. Pat. No. 5,028,787 and, as a consequence, it is possible to provide the necessary accuracy in glucose determination using a simpler concentration calculation algorithm. On the other hand, in the wavelength selection and corresponding calculation algorithm, the reference wavelength is selected so that the reflectance of the light is substantially unaffected by the concentration of a blood component and a signal wavelength is selected among infrared wavelengths at which the reflectance varies with the concentration of a blood component being measured. Their corresponding electrical signal ratio is not sufficient for accurate determination of blood glucose concentration taking into account blood and tissue components which absorb light in this spectral range. It is necessary to keep in mind a possibility that when other components (not glucose) of blood change their concentration, it will cause a change in the reflectance on the wavelength selected for glucose measurement.

It should be noted that only Braig et al. (U.S. Pat. No. 5,313,941) emphasizes the advantages of pulsed near infrared light source for blood glucose determination. However, Braig et al. uses broadband pulses of infrared light which are emitted in the range of 2–20 μm and are synchronized with the systole and diastole of the patient cardiac cycle. At the same time, it is possible to point out the evident advantages of pulsed polychromatic light source such as a Xe flash lamp. Flash lamp light sources have higher peak power than Light-Emitting Diodes and in comparison with known laser diodes, the main advantage is that a pulsed flash lamp provides a continuous spectrum. As a consequence, selecting any wavelength is possible and, they are not as expensive as laser diodes. Moreover, pulsed flash lamps can be significantly smaller than polychromatic light sources such as quartz-halogen or tungsten-halogen bulb.

Therefore, it is possible to develop compact personal monitoring device based on a pulsed flash lamp. This kind of device was proposed by A. Yamanishi (U.S. Pat. No. 4,267,844) for measurement of bilirubin concentration using a two wavelength algorithm (one wavelength is selected as a signal corresponding to the absorption of bilirubin and the other was selected as a reference signal corresponding to the background absorption). A noninvasive device for cholesterol measurement is also known in U.S. Pat. No. 5,246,004 where the light of a plurality of discrete wavelengths selected from the near infrared spectrum is used to illuminate the blood and the above-mentioned algorithm using the ratio of the signal and a background reference signal is used.

One of the main disadvantages in biomedical applications of near infrared reflectance spectroscopy, as described above, is variations in the spectral baseline. For example, in recent investigations aimed at transcutaneous glucose monitoring, baseline variations in spectra were found to overwhelm the spectral features associated with glucose absorption. The scattering coefficient of biological tissue depends on many structural fibers and the shapes and sizes of cellular structures. To obtain reproducible absorption data from the near infrared reflectance spectroscopy, one must minimize the effects of changes in the scattering background.

Thus, there is a great need for a method and device for noninvasive blood glucose concentration measurement which provide reliable and accurate results.

SUMMARY OF THE INVENTION

To solve the above and other problems, it is an objective of the present invention to provide a convenient, reliable and accurate method for measuring blood components, such as glucose concentrations in a noninvasive manner.

It is another objective of the present invention to provide a convenient, reliable and accurate device for measuring blood glucose concentrations in a noninvasive manner.

Accordingly, to achieve these and other objectives, there is provided a method for measuring blood component concentrations including the steps of (a) supplying power to a light source, a microprocessor, photodetectors, pre-amplifiers, analog-to-digital converters and a display, (b) emitting near infrared light in the spectral region of 800–1850 nm by the light source, (c) focusing the near infrared light by a reflector and a condenser to irradiate the focused light on the skin of a subject, (d) receiving the near infrared light, containing information on the blood component concentration, back scattered from or transmitted through blood-containing tissues and blood vessels, by a plurality of directing elements to be directed to spectral selective elements, (e) selectively outputting the light of at least three wavelengths from the near infrared light by the spectral selective elements, (f) converting the light of at least three wavelengths output from the spectral selective elements into analog electrical signals, respectively, (g) amplifying the analog electrical signals by pre-amplifiers, (h) converting the amplified analog electrical signals into digital signals by the analog-to-digital converters and transmitting the same to the microprocessor, (i) calculating a ratio D of the digital signals, represented by the following formula $$D = (\log 1/T_1 - \log 1/T_2) \bigg/ \left[ \sum_{i=3}^{n} (\log 1/T_{i-1}) - (n-2)\log 1/T_n \right],$$

where n is the number of selected wavelengths, so that for n=3, $D$=(log $1/T_1$–log $1/T_2$)/(log $1/T_2$–log $1/T_3$), and for n=4, $D$=(log $1/T_1$–log $1/T_2$)/(log $1/T_2$+log $1/T_3$–2 log $1/T_4$), (j) comparing the calculated ratio D with a calibration curve stored in a memory, and calculating the blood component concentration by the microprocessor and (k) displaying the blood component concentration calculated by the microprocessor on the display, wherein $T_i = J_i/J_{io}$, where i=1, 2, . . . , n, $J_i$ and $J_{io}$ are intensities of the back scattered or transmitted light and incident light corresponding to the wavelength i, respectively.

In step (b), the near infrared light in the range of 800–1850 nm is simultaneously irradiated on the blood-containing tissues and blood vessels through skin during a predetermined time pulse interval.

Also, in step (d), the plurality of directing elements are oriented and spatially separated to avoid direct reflection from the skin surface and to provide minimization of the effects of changes in the scattering background.

Also, in step (e), assuming that $A_{ic}$, i=1, 2, . . . , n are absorption values of light of n wavelengths for determining a blood component c and $A_{ij}$, i=1, 2, . . . , n are absorption values of the light of n wavelengths for other components with the exception of the blood component to be determined, $A_{2C}, A_{3C}, \ldots, A_{nC}$ are negligible compared to $A_{1C}$, and the light of n wavelengths are utilized for other components with the exception of the determining blood component, satisfying the relation $$A_{1j} - A_{2j} \approx \sum_{i=3}^{n} (A_{(i-1)j}) - (n-2)A_{nj},$$

so that for n=3, $A_{1j}-A_{2j} \approx A_{2j}-A_{3j}$, and for n=4, $A_{1j}-A_{2j} \approx A_{2j}+A_{3j}-2A_{4j}$.

Also provided is a device for measuring blood component concentrations including a near infrared light source for emitting light in the spectral range of 800–1850 nm, a reflector for reflecting the near infrared light generated at the infrared light source, a condenser for collecting and focusing near infrared light and irradiating the same onto the skin of a subject, directing elements for receiving the near infrared light, containing information on blood component concentrations, back scattered from or transmitted through the blood-containing tissues and blood vessels, and directing the same to other directions, spectral selective elements for selectively outputting the light of at least three wavelengths from the near infrared light, photodetectors for receiving the respective optical signals selectively output from said spectral selective elements and converting the optical signals into analog electrical signals, pre-amplifiers for amplifying the respective analog electrical signals output from the photodetectors, analog-to-digital converters for converting the amplified analog electrical signals into digital signals, a microprocessor for calculating a ratio D represented by a predetermined formula, that is, $$D = (\log 1/T_1 - \log 1/T_2) \bigg/ \left[ \sum_{i=3}^{n} (\log 1/T_{i-1}) - (n-2)\log 1/T_n \right],$$

where n is the number of selected wavelengths, so that for n=3, $D$=(log $1/T_1$–log $1/T_2$)/(log $1/T_2$–log $1/T_3$), and for n=4, $D$=(log $1/T_1$–log $1/T_2$)/(log $1/T_2$+log $1/T_3$–2log $1/T_4$), comparing the ratio D with a calibration curve stored in a memory, and calculating blood component concentrations, a display for displaying the blood component concentrations calculated by the microprocessor and a power source for supplying power to the infrared light source, the microprocessor, the photodetectors, the pre-amplifiers, the analog-to-digital converters, and the display, wherein $T_i = J_i/J_{io}$ where i=1, 2, . . . , n, $J_i$ and $J_{io}$ are intensities of the back scattered or transmitted light and incident light, correspond wavelength i, respectively.

The near infrared light source is preferably a flash lamp providing simultaneous irradiation of the blood-containing tissues and blood vessels through skin during a predetermined time pulse interval.

Also, the near infrared light source is preferably either a light emitting diode or a laser diode.

Also, the directing elements preferably include properly oriented and spatially separated right angle prisms to avoid surface reflection from the skin and provide minimization of the effects of changes in the scattering background.

Further, the directing elements preferably include optical fiber bundles.

The directing elements and the spectral selective elements preferably include dispersion prisms.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention. In the drawings:

FIG. 1 is a plot of absorption spectra for water, glucose, hemoglobin, cholesterol, albumin, alcohol, skin, fat and muscle in the 800–1800 nm spectral region;

FIG. 2b is a side view of the device for measuring blood glucose along section B—B in FIG. 2a viewed from a direction marked by A; and FIG. 3 is a flow chart illustrating a method for measuring blood component concentrations according to the embodiment of the present invention.

DESCRIPTION OF THE PREFERRED EMBODIMENTS

Figure 2A:
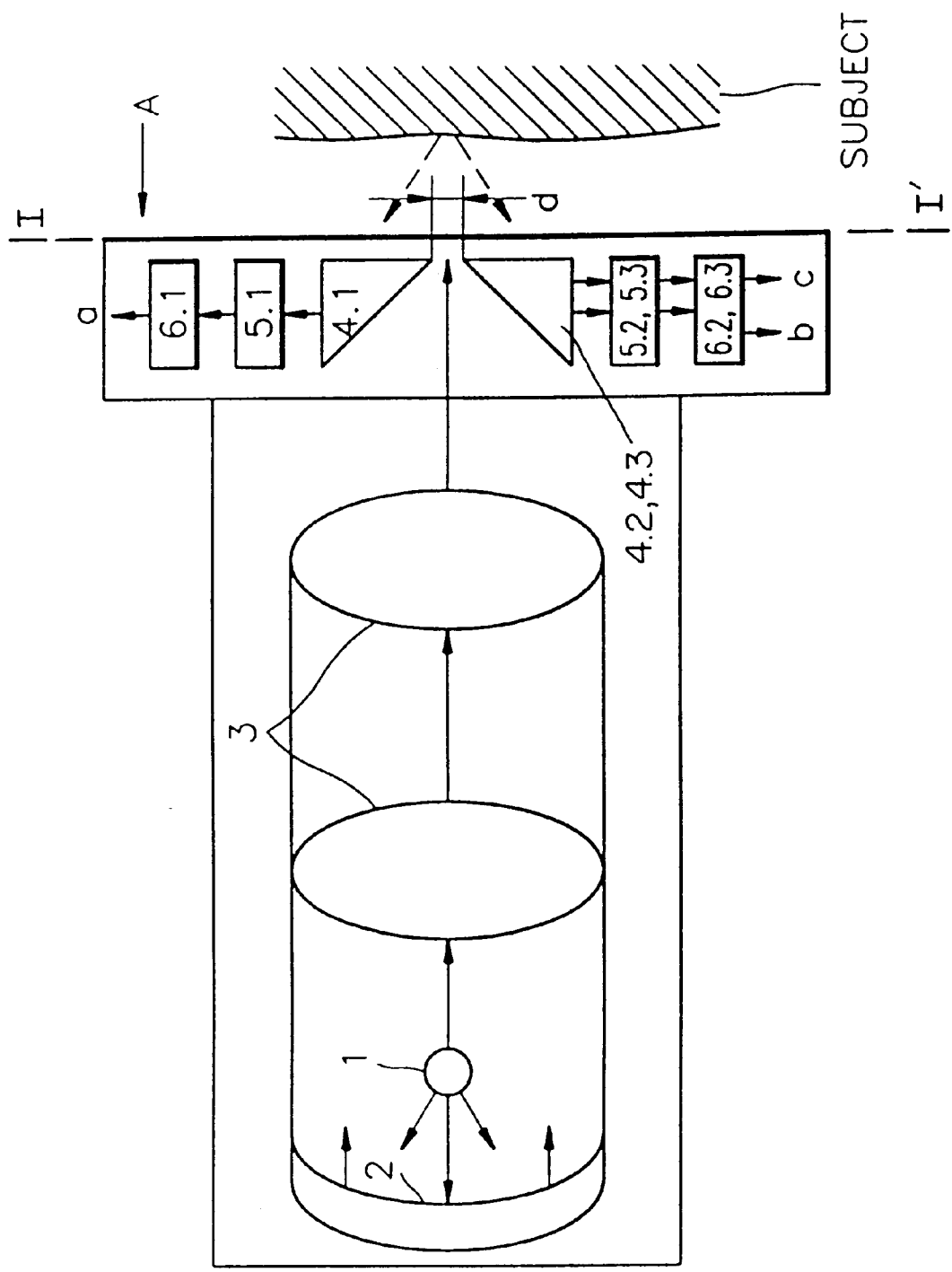
FIG. 2a is a block diagram illustrating a device for measuring blood component concentrations according to the embodiment of the present invention.

The present invention provides a method and device for noninvasive measurement of blood component concentrations which will be described with reference to accompanying drawings. In this embodiment glucose concentration is measured using light of three wavelengths.

The present invention relates to a method and device for detecting and quantifying blood component concentration levels noninvasively by using a pulsed polychromatic light source that emits a broad spectrum of light, in particular, in a near infrared range, to illustrate a patient's bodily tissue.

Light illuminated on the tissue penetrates through the tissue in particular to the blood vessels where the light interacts with glucose molecules. It should be noted that glucose is concentrated not only in blood but also in surrounding blood vessel tissues because the small molecular weight glucose molecules penetrate and diffuse into the tissue. Of course, the concentration of glucose in the tissues is proportional to the concentration of glucose in blood. Therefore, it is not necessary to localize the transmitting channel of the instrument in the region around a blood vessel. The back scattered light from blood and blood-contianing tissues will be decreased by the characteristic absorption of the glucose molecules and, therefore, has information about the glucose concentration in the blood.

The analysis method included in the present invention can be described by multi-wavelengths normalized ratio algorithm taking into account that there are many components of blood and blood-containing tissues which have absorption in the near infrared region. The main components are water, hemoglobin, albumin, cholesterol, skin, fat, muscles, glucose, etc. Spectra of some of these components and constituents in near infrared region are shown in FIG. 1. Total absorption $A_i$ of the light in this case is the sum of absorption values of the components on selected wavelengths, i.e., $$A_i = \sum_j A_{ij},$$

where i is an index of a corresponding wavelength, and j is an index of the blood components (water, hemoglobin, cholesterol, skin, fat, albumin and glucose, etc.).

The simplest example is the case of transmission and its main principle is true of reflection. For n wavelengths it is possible to define the ratio (D) as follows:

$$D = (\log 1/T_1 - \log 1/T_2) \bigg/ \left[ \sum_{i=3}^{n} (\log 1/T_{i-1}) - (n-2)\log 1/T_n \right] \quad (1)$$

$$= \sum_j (A_{1j} - A_{2j}) \bigg/ \sum_j \left[ \sum_{i=3}^{n} (A_{(i-1)j}) - (n-2)A_{nj} \right]$$

For the case of n=3, $$D = (\log 1/T_1 - \log 1/T_2)/(\log 1/T_2 - \log 1/T_3) \quad (2)$$

$$= \sum_j (A_{1j} - A_{2j}) \bigg/ \sum_j (A_{2j} - A_{3j})$$

For the case of n=4, $$D = (\log 1/T_1 - \log 1/T_2)/(\log 1/T_2 + \log 1/T_3 - 2\log 1/T_4) \quad (3)$$

$$= \sum_j (A_{1j} - A_{2j}) \bigg/ \sum_j (A_{2j} - 2A_{4j} + A_{3j})$$

where $$T_i = \text{Exp}\left(-\sum_j A_{ij} l\right),$$

assuming that $A_{ij}$ is an absorption value of the light of the component j for the wavelength i and $\ell$ is a light path length in blood-containing tissues and in blood vessels. Above mentioned Equations 1 through 3 provide a minimum number of selected wavelengths and at the same time significant compensation for the change of the D value by the influence of the varying concentration of the other main blood components.

Selection of three wavelengths is reasonable to minimize the number of receiving channels, and the requirements for wavelengths selection are:

a) $A_{1g}$ is the maximum among $A_{1g}$, $A_{2g}$ and $A_{3g}$, and $A_{2g}$ and $A_{3g}$ are negligible when compared to $A_{1g}$; and b) for other components, with the exception of glucose, the relation $A_{1j} - A_{2j} \approx A_{2j} - A_{3j}$ must be satisfied.

Selection of four wavelengths provides a more significant compensation of the influence of the other components on the value when there are variations in their concentrations. Corresponding requirements for the wavelengths selection are:

a) $A_{1g}$ is the maximum among $A_{1g}, A_{2g}, A_{3g}$ and $A_{4g}$, and $A_{2g}, A_{3g}$, and $A_{4g}$ are negligible when compared to $A_{1g}$; and (b) for other components, with the exception of glucose, the relation $A_{1j}-A_{2j} \approx A_{2j}+A_{3j}-2A_{4j}$ must be satisfied to compensate for dominant blood components (water, hemoglobin) on the D value.

In the case of selection of n wavelengths the requirements for wavelengths selection are:

(a) $A_{1g}$ is the maximum among $A_{1g}, A_{2g}, \ldots, A_{ng}$ and $A_{2g}, A_{3g}, \ldots, A_{ng}$ are negligible when compared to $A_{1g}$; and (b) for other components, with the exception of glucose, the relation $$A_{1j} - A_{2j} \approx \sum_{i=3}^{n} (A_{(i-1)j}) - (n-2)A_{nj}$$

must be satisfied to compensate for dominant blood components.

On account of these conditions, the formula for glucose concentration $C_g$ can be written as follows:

$$C_g = K_0 + K_1 D, \quad (4)$$

$$K_0 = -\varepsilon_g^{-1} \sum_j (A_{1j} - A_{2j}),$$

$$K_1 = \varepsilon_g^{-1} \left\{ \sum_j \left[ \sum_{i=3}^{n} (A_{(i-1)j}) - (n-2)A_{nj} \right] \right\}$$

For the case of n=3, $$K_1 = \varepsilon_g^{-1} \sum_j (A_{2j} - A_{3j})$$

and for the case n=4, $$K_1 = \varepsilon_g^{-1} \sum_j (A_{2j} + A_{3j} - 2A_{4j}),$$

where $K_0$ and $K_1$ are the intercept and the line slope and these are determined by a calibration procedure which is within the ability of one skilled in the art. In this case, the sums do not include the component to be determined. Moreover, since in the real case the (a) and (b) requirements for the wavelengths selection cannot be provided for all the components with the same efficiency, sometimes it is reasonable to apply three or four wavelength algorithms for different blood components simultaneously an using optimal set of wavelengths corresponding to each component.

In this case interference compensation will be more efficient because of the possibility of using data obtained from another component set and its corresponding equation. For example, selecting a different wavelength set for each of cholesterol, albumin, hemoglobin and determining their concentrations will make it possible to apply new concentration data for the determination of the glucose concentration on the basis of the next corresponding glucose wavelength set (Equation 5).

$$\Delta D = \sum_j d_j \Delta x_j \quad (5)$$

where $\Delta X_j = \Delta C_j/C_{jo}$, relative ratio of initial concentration $C_{jo}$ in calculation procedure and the concentration variation $\Delta C_j$ thereof and $d_j$ is the line slope with respect to each concentration variation. It is possible to provide the number of equations (wavelength set) equal to the number of unknown variables ($\Delta X_j$) in order to find the concentrations of all blood components with absorption in the near infrared range. At the same time it is possible to exclude some components from consideration using appropriately selected wavelength algorithms.

According to the above-described algorithm, the infrared light of three wavelengths such as 1625 nm, 1364 nm and 1200 nm can preferably be used and the infrared light of four wavelengths such as 1625 nm, 1364 nm, 1200 nm and 1300 nm can preferably be used for measurements of glucose. Also, according to the Equation 5, the infrared light of wavelength set 1164 nm, 1225 nm, 1300 nm is used for determining hemoglobin concentration and after that the infrared light of wavelength sets {1718 nm, 1364 nm, 1300 nm, 1164 nm} and {1739 nm, 1364 nm, 1300 nm, 1164 nm} can be used for determining cholesterol and albumin concentrations using the determined hemoglobin concentration, respectively, and finally the infrared light of wavelength set 1625 nm, 1364 nm, 1225 nm and 1164 nm can be used for determining blood glucose concentration using the determined concentrations of hemoglobin, cholesterol and albumin.

However, the above set of optimal wavelengths is only one example, not limited to the wavelengths described in the previous paragraph. Depending on the studies of absorption spectra for the related blood components, the values of wavelengths may be different.

FIGS. 2a and 2b are block diagrams illustrating a device for measuring blood component concentrations using the light of three wavelengths according to the embodiment of the present invention and FIG. 3 is a flow chart illustrating a method for measuring blood component concentrations according to the embodiment of the present invention.

As shown in FIGS. 2a and 2b, the device for noninvasive measurement of blood component concentrations includes a near infrared light source 1 for emitting light in the spectral range 800–1850 nm, an optical reflector 2 for reflecting the near infrared light generated at the infrared light source 1, a condenser 3 for collecting and focusing the near infrared light and irradiating the same onto the skin of a subject, first through third directing elements 4.1, 4.2 and 4.3 for receiving the near infrared light containing the information on blood glucose concentration, back scattered from the blood-containing tissues and blood vessels and directing the same to other directions, first through third spectral selective elements 5.1, 5.2 and 5.3 for selectively outputting light of three wavelengths from the near infrared light, first through third photodetectors 6.1, 6.2 and 6.3 for receiving the respective optical signals from the first through third spectral selective elements 5.1, 5.2 and 5.3 and converting the optical signals into analog electrical signals, first through third pre-amplifiers 7.1, 7.2 and 7.3 for amplifying the respective analog electrical signals output from the first through third photodetectors 6.1, 6.2 and 6.3, first through third analog-to-digital (A/D) converters 8.1, 8.2 and 8.3 for converting the amplified analog electrical signals into digital signals, a microprocessor 9 for calculating a ratio (D) represented by a predetermined formula, comparing the same with a calibration curve stored in a memory 10, and calculating blood glucose concentration, a display 11 for displaying the blood glucose concentration calculated by the microprocessor 9, and a power source 12 for supplying power to the infrared light source 1, the microprocessor 9, the first through third photodetectors 6.1, 6.2 and 6.3, the first through third pre-amplifiers 7.1, 7.2 and 7.3, the first through third analog-to-digital (A/D) converters 8.1, 8.2 and 8.3, and the display 11.

The near infrared light source 1 is a polychromatic light source that emits light in a wide bandwidth which includes light in the near infrared range. The power can be supplied by a stabilized power supply source such as a DC power supply or by a battery. The power source 12 for supplying power to the infrared light source 1, the microprocessor 9, the first through third photodetectors 6.1, 6.2 and 6.3, the first through third pre-amplifiers 7.1, 7.2 and 7.3, the first through third analog-to-digital (A/D) converters 8.1, 8.2 and 8.3, and the display 11 are electrically connected thereto. The connections of the power source 10 are not shown in FIG. 2b as they are within the ability of one skilled in the art.

The near infrared light source 1 is optically connected and adjusted with respect to the optical reflector 2 and the optical condenser 3 which is a set of specially selected and adjusted lenses to provide effective focusing of the light beam. The light from the near infrared light source 1 is reflected from the optical reflector 2 and is directed to the condenser 3. The condenser 3 focuses the light beam on the surface of the skin. Any part of the human body can be used as a subject, for example, the finger, wrist or ear. Back scattered light from blood-containing tissues is directed to the spectral selective elements 5. 1, 5.2 and 5.3 by three corresponding directing elements 4.1, 4.2 and 4.3,. At the same time, the light reflected from the skin surface is not directed to the first through third spectral selective elements 5.1, 5.2 and 5.3 by the location and orientation of the first through third directing elements 4.1, 4.2 and 4.3. Prisms, fiber bundles, dispersing elements can be used as the first through third directing elements 4.1, 4.2 and 4.3. The distance (2/d, d is usually 2–5 mm) between the edge of the directing elements and focal point location is sufficient to avoid direct reflection from the skin surface and at the same time is optimal for providing minimization of the effects of changes in the scattering background. The first through third spectral selective elements 5.1, 5.2 and 5.3 selectively output narrow spectral light from the near infrared region. The light output from the first through third spectral selective elements 5.1, 5.2 and 5.3 is input to the first through third photodetectors 6.1, 6.2 and 6.3 which are sensitive in the near infrared region. Preferably, germanium photodiodes can be used as the photodetectors.

The method and device for noninvasive measurement of blood component concentrations according to the embodiment of the present invention will be described with reference to FIGS. 2a, 2b and 3.

If the power source 12 supplies power to various parts in step 30, the near infrared light source 1 illuminates with near infrared light in step 32. In step 34, the infrared light reflected from the optical reflector 2 is focused and then irradiated onto the skin of the subject. In step 36, the near infrared light containing information on blood glucose concentration, back scattered from the blood-containing tissues and blood vessels, is received by the first through third directing elements 4.1, 4.2 and 4.3 and is transmitted to the first through third spectral selective elements 5.1, 5.2 and 5.3.

In step 38, the light of three wavelengths is selected from the near infrared light by the first through third spectral selective elements 5.1, 5.2 and 5.3 and then output to the first through third photodetectors 6.1, 6.2 and 6.3. In step 40, the light input by the first through third photodetectors 6.1, 6.2 and 6.3 is converted into analog electrical signals. In step 42, the respective analog electrical signals are amplified by the first through third preamplifiers 7.1, 7.2 and 7.3 electrically connected to the first through third photodetectors 6.1, 6.2 and 6.3. In step 44, the analog electrical signals output from the first through third preamplifiers 7.1, 7.2 and 7.3 are converted into digital signals by the first through third A/D converters 8.1, 8.2 and 8.3. In step 46, data output from the first through third A/D converters 8.1, 8.2 and 8.3 are input to the microprocessor 9. The microprocessor 9 calculates a ratio (D) of the digital signals, represented by the above-described formula (1), compares the calculated ratio (D) with a calibration curve stored in the memory 10, and calculates blood glucose concentration. Here, in step 46 the concentrations of blood components also can be calculated according to chemometric analysis. In step 48, the calculated blood glucose concentration is displayed on the display 11 connected to the microprocessor 9.

The near infrared light source 1 can be a flash lamp. Also, it is possible to use any light source which is sufficiently intensive and emits light on selected wavelengths such as corresponding LEDs or laser diodes. Also, the microprocessor 9 can be a one-chip microcomputer including an analog-to-digital converter and a memory.

It is clear that above proposed description can be applied for the case of four wavelength algorithm or a combination of four-and three-wavelength algorithms or in general for the case of an n-wavelength algorithm. Also, it is clear that the present invention can be applied to the measurement of concentrations of cholesterol, albumin, hemoglobin and bilirubin and some other analytes like alcohol and drugs as well as the concentration of blood glucose.

As described above, in the method and device for non-invasive measurement of concentrations of blood components according to the present invention, the device can be used without discomfort to the patient and requires minimal cost. Also, it is possible to quickly measure blood component concentration at home. Also, according to the present invention, pain to the patient and danger of infection due to frequent blood-gathering can be avoided. Further, in the present invention, to increase the accuracy of the measurement of reflectivity of near infrared light in human body tissues, the effects of changes in the back scattering background should be minimized. Also, to avoid reflection from the skin surface to the received channels, transmission and reception channels are spatially separated from each other. Minimization of the effects of changes in the back scattering background can be attained by taking measurements at a predetermined distance, preferably 2–5 mm, spaced from the irradiation point. This can be implemented for example, by using spatially separated fiber bundles or right angle prisms.

Other embodiments of the invention will be apparent to those skilled in the art from a consideration of the specification and practice of the invention disclosed herein. It is intended that the specification be considered as exemplary only, with the true scope and spirit of the invention being indicated by the following claims.

What is claimed is:

1. A method for measuring concentrations of blood components and analytes including at least one of glucose, cholesterol, albumin, hemoglobin, alcohol or drugs, the method comprising the steps of:

(a) irradiating near infrared light onto skin of a subject containing blood-containing tissues and blood vessels;

(b) receiving the near infrared light containing information on the blood component concentration, back scattered from or transmitted through the blood-containing tissues and blood vessels;

(c) selectively outputting the light of at least three wavelengths from the received near infrared light;

(d) converting the light of the at least three outputted wavelengths electrical signals, respectively; and (e) computing the blood component concentration using the electrical signals, wherein in step (c), assuming that $A_{ic}$, i=1, 2, ..., n, are absorption values of light of n wavelengths for the blood component being measured, the requirements for selection of the wavelengths are:

(1) $A_{1c}$ is the maximum among $A_{1c}, A_{2c}, A_{3c}, \ldots, A_{nc}$, and $A_{2c}, A_{3c}, \ldots, A_{nc}$ are negligible when compared to $A_{1c}$; and (2) for other components, with the exception of the blood component being measured, the relation $$A_{1j} - A_{2j} \approx \sum_{i=3}^{n}(A_{(i-1)j}) - (n-2)A_{nj}$$

is satisfied, where $A_{ij}$ is absorption value of wavelength i for blood component j, and n is the number of selected wavelengths.

2. The method according to claim 1, wherein in step (a), the near infrared light in the range of 800–1850 nm is simultaneously irradiated on the blood-containing tissues and blood vessels through skin during a predetermined time pulse interval.

3. The method according to claim 1, wherein step (a) of irradiating uses irradiation channels and step (b) of receiving the near infrared light uses reception channels that are spatially separated from the irradiation channels to avoid direct reflection from the skin surface.

4. The method according to claim 1, wherein in step (c) assuming that $A_{ic}$, i=1, 2, 3, are absorption values of light of three wavelengths 1, 2, and 3 for the blood component being measured the requirements for selection of the wavelengths are:

(1) $A_{1c}$ is the maximum among $A_{1c}, A_{2c}, A_{3c}$, and $A_{2c}, A_{3c}$ are negligible when compared to $A_{1c}$; and (2) for other components, with the exception of the blood component being measured, the relation $A_{ij}-A_{2j}\approx A_{2j}-A_{3j}$ is satisfied, where $A_{ij}$ is absorption value of wavelength i for blood component j.

5. The method according to claim 4, wherein the wavelengths 1, 2 and 3 are 1625 nm, 1364 nm and 1200 nm, respectively.

6. The method according to claim 1, wherein in step (c), assuming that $A_{ic}$, i=1, 2, 3, 4, are absorption values of light of four wavelengths 1, 2, 3, and 4 for the blood component being measured the requirements for selection of the wavelengths are:

(1) $A_{1c}$ is the maximum among $A_{1c}, A_{2c}, A_{3c}, A_{4c}$, and $A_{2c}, A_{3c}$, and $A_{4c}$ are negligible when compared to $A_{1c}$; and (2) for other components, with the exception of the blood component being measured, the relation $A_{1j}-A_{2j}\approx A_{2j}+A_{3j}-2A_{4j}$ is satisfied, where $A_{ij}$ is absorption value of wavelength i for blood component j.

7. The method according to claim 6, wherein the wavelengths 1, 2, 3 and 4 are 1625 nm, 1364 nm, 1200 nm and 1300 nm, respectively.

8. The method according to claim 1, wherein the steps (a) through (e) are repeated to determine concentrations of other blood components using wavelength sets corresponding to a respective optimal wavelength set for each of the other blood component and applying all of the determined concentrations to make a more accurate determination of finally determined blood component concentrations.

9. The method according to claim 8, wherein the steps (a) through (e) are repeated using a wavelength set of 1164 nm, 1225 nm, 1300 nm for determining hemoglobin concentration and thereafter using a first wavelength set (1718 nm, 1364 nm, 1300 nm, 1164 nm) and a second wavelength set (1739 nm, 1364 nm, 1300 nm, 1164 nm) for determining cholesterol and albumin concentrations, respectively, using the determined hemoglobin concentration and finally using a third wavelength set (1625 nm, 1364 nm, 1225 nm and 1164 nm) for determining blood glucose concentration using the determined concentrations of hemoglobin, cholesterol and albumin.

10. The method according to claim 1, wherein step (e) of computing the blood component concentration includes using a chemometric analysis applied to the calculation of to calculate the blood component concentrations.

11. A device for measuring blood component concentrations comprising:

means for irradiating near infrared light onto skin of a subject containing blood-containing tissues and blood vessels;

means for receiving the near infrared light containing information on the blood component concentration, back scattered from or transmitted through blood-containing tissues and blood vessels;

means for selectively outputting the light of at least three wavelengths from the received near infrared light;

means for converting the light of the at least three output wavelengths into electrical signals, respectively, and means for computing the blood component concentration using the electrical signals;

wherein assuming that $A_{ic}$, i=1, 2 ..., n, are absorption values of light of n wavelengths for the blood component being measured the requirements for wavelengths selection are:

(1) $A_{1c}$ is the maximum among $A_{ic}, A_{2c}, A_{3c}, \ldots, A_{nc}$, and $A_{2c}, A_{3c}, \ldots, A_{nc}$ are negligible when compared to $A_{1c}$, and (2) for other components, with the exception of the blood component being measured, the relation $$A_{1j} - A_{2j} \approx \sum_{i=3}^{n}(A_{(i-1)j}) - (n-2)A_{nj}$$

is satisfied, where $A_{ij}$ is absorption value of wavelength i for blood component j and n is the number of selected wavelengths.

12. The device according to claim 11, wherein the computing means calculates a ratio D of the electrical signals, represented by the following formula $$D = (\log 1/T_1 - \log 1/T_2) / \left[\sum_{i=3}^{n}(\log 1/T_{i-1}) - (n-2)\log 1/T_n\right].$$

compares the calculated ratio D with a predetermined calibration curve, and calculates the blood component from the comparison of the calculated ratio D with the predetermined calibration curve, wherein $T_i=J_i/J_{io}$ where i=1, 2, ..., n, $J_i$ and $J_{io}$ are intensities of the back scattered or transmitted light and incident light corresponding to the wavelength i, respectively.

13. The device according to claim 11, wherein the irradiating means is a flash lamp providing simultaneous irradiation of the blood-containing tissues and blood vessels through skin during a predetermined time pulse interval.

14. The device according to claim 11, wherein the irradiating means is a light emitting diode.

15. The device according to claim 11, wherein the irradiating means is a laser diode.

16. The device according to claim 11, wherein the receiving means includes spatially separated right angle prisms oriented to avoid surface reflection from the skin.

17. The device according to claim 11, wherein the receiving means includes optical fiber bundles.

18. The device according to claim 11, wherein the receiving means and the selective outputting means include dispersion prisms.

19. A method for measuring concentrations of blood components and analytes including at least one of glucose, cholesterol, albumin, hemoglobin, alcohol and drugs, the method comprising the steps of:
(a) irradiating near infrared light onto skin of a subject containing blood-containing tissues and blood vessels;
(b) receiving the near infrared light containing information on the blood component concentration, back scattered from or transmitted through blood-containing tissues and blood vessels;
(c) selectively outputting the light of at least three wavelengths from the received near infrared light;
(d) converting the light of the at least three output wavelengths into electrical signals, respectively;
(e) calculating a ratio D using the electrical signals, represented by the following formula $$D = (\log 1/T_1 - \log 1/T_2) / \left[\sum_{i=3}^{n} (\log 1/T_{i-1}) - (n-2)\log 1/T_n\right],$$

wherein $T_i=J_i/J_{io}$, where i=1, 2, ..., n, $J_i$ and $J_{io}$ are intensities of the back scattered or transmitted light and incident light, corresponding to the wavelength i, respectively; and
(f) calculating blood component concentration using the calculated ratio D.

20. The method according to claim 19, wherein step (f) is performed by comparing the calculated ratio D with a predetermined calibration curve.

21. The method according to claim 19, wherein in step (c) the light of three wavelengths from the near infrared light is selectively output and in step (d) the light of three wavelengths output is converted into the electrical signals, respectively, and in step (e) the ratio D using the electrical signals, represented by the following formula $D=(\log 1/T_1 - \log 1/T_2)/(\log 1/T_2 - \log 1/T_3)$, wherein $T_i=J_i/J_{io}$, where i=1, 2, 3, $J_i$ and $J_{io}$ are intensities of the back scattered or transmitted light and incident light, corresponding to the wavelength i, respectively.

22. The method according to claim 19, wherein in step (c) the light of four wavelengths from the near infrared light is selectively output and in step (d) the light of four wavelengths output is converted into the electrical signals, respectively, and in step (e) the ratio D using the electrical signals, represented by the following formula $D=(\log 1/T_1 - \log 1/T_2)/(\log 1/T_2 + \log 1/T_3 - 2\log 1/T_4)$, wherein $T_i=J_i/J_{io}$, where i=1, 2, 3, 4, $J_i$ and $J_{io}$ are intensities of the back scattered or transmitted light and incident light, corresponding to the wavelength i, respectively.

23. A device for measuring blood component concentrations comprising:
means for irradiating near infrared light onto skin of a subject containing blood-containing tissues and blood vessels;
means for receiving the near infrared light containing information on the blood component concentration, back scattered from or transmitted through blood-containing tissues and blood vessels;
means for selectively outputting the light of at least three wavelengths from the received near infrared light;
means for converting the light of the at least three output wavelengths into electrical signals, respectively; and
means for computing the blood component concentration using the electrical signals, wherein the means for irradiating includes irradiation channels and the means for receiving includes reception channels, the irradiation channels and the reception channels being spatially separated and said receiving means is spaced from an irradiation point by a predetermined distance.

24. The device according to claim 23, wherein the predetermined distance is about 2–5 mm.

* * * * *